US00PP34681P2

(12) United States Plant Patent
Eckenberg et al.

(10) Patent No.: US PP34,681 P2
(45) Date of Patent: Oct. 25, 2022

(54) CHERRY TREE NAMED 'RL 100'

(50) Latin Name: *Prunus avium*
Varietal Denomination: RL 100

(71) Applicant: Richard W. Leitz, Mattawa, WA (US)

(72) Inventors: Audra Elizabeth Eckenberg, Mattawa, WA (US); Richard W. Leitz, Mattawa, WA (US)

(73) Assignee: Richard W. Leitz

( * ) Notice: Subject to any disclaimer, the term of this patent is extended or adjusted under 35 U.S.C. 154(b) by 0 days.

(21) Appl. No.: 17/803,099

(22) Filed: Feb. 4, 2022

(51) Int. Cl.
*A01H 5/08* (2018.01)
*A01H 6/74* (2018.01)

(52) U.S. Cl.
USPC ..... Plt./181
CPC ..... *A01H 6/7445* (2018.05)

(58) Field of Classification Search
USPC ..... Plt./181
CPC ..... A01H 6/7445; A01H 5/08
See application file for complete search history.

*Primary Examiner* — Keith O. Robinson
(74) *Attorney, Agent, or Firm* — Michelle Bos Legal LLC

(57) ABSTRACT

A new cherry tree notable for its attractive red fruit, which has a pleasant sub-acid flavor and matures early in the season.

4 Drawing Sheets

Latin name: *Prunus avium.*
Variety denomination: 'RL 100'.

BACKGROUND OF THE VARIETY:

'RL 100' is a new and distinct variety of sweet cherry tree discovered as a whole tree mutation in an established cherry orchard near Mattawa, Wash. in 2013. Other varieties near the orchard include 'Rainier', 'Lapin' and 'Bing' (all unpatented), and 'Sonata' (U.S. Plant Pat. No. 11,378). Parentage of 'RL 100' is unknown. 'RL 100' was first asexually propagated by bud grafting at Mattawa in 2014, and has since been observed to remain true to type through successive asexually propagated generations.

BRIEF DESCRIPTION OF THE VARIETY

The 'RL 100' cherry tree is distinguished by its attractive red fruit, which has a pleasant sub-acid flavor and matures early in the season. Table 1 shows a comparison of 'RL 100' to 'Rainier' and 'Sonata'.

TABLE 1

| Characteristic | 'RL 100' | Rainier | Sonata |
|---|---|---|---|
| Fruit flesh color | Yellow-orange | Yellow | Dark magenta |
| Fruit skin color | Red-purple with red speckles | Yellow with orange to red blush | Dark mahogany |
| Fruit flavor | Sub-acid, sweet; 20 to 26 Brix | Sweet, bland; 18 to 22 Brix | Acid, vegetal |
| Harvest maturity | Early season; early to mid-June | Mid-season; mid- to late June | Mid- to late season; late June |

BRIEF DESCRIPTION OF THE PHOTOGRAPHS

The accompanying photographs were obtained in 2013, 2014 and 2015 at Mattawa, Wash. The trees depicted were planted in 2013.

DETAILED BOTANICAL DESCRIPTION OF THE VARIETY

Figure 1:
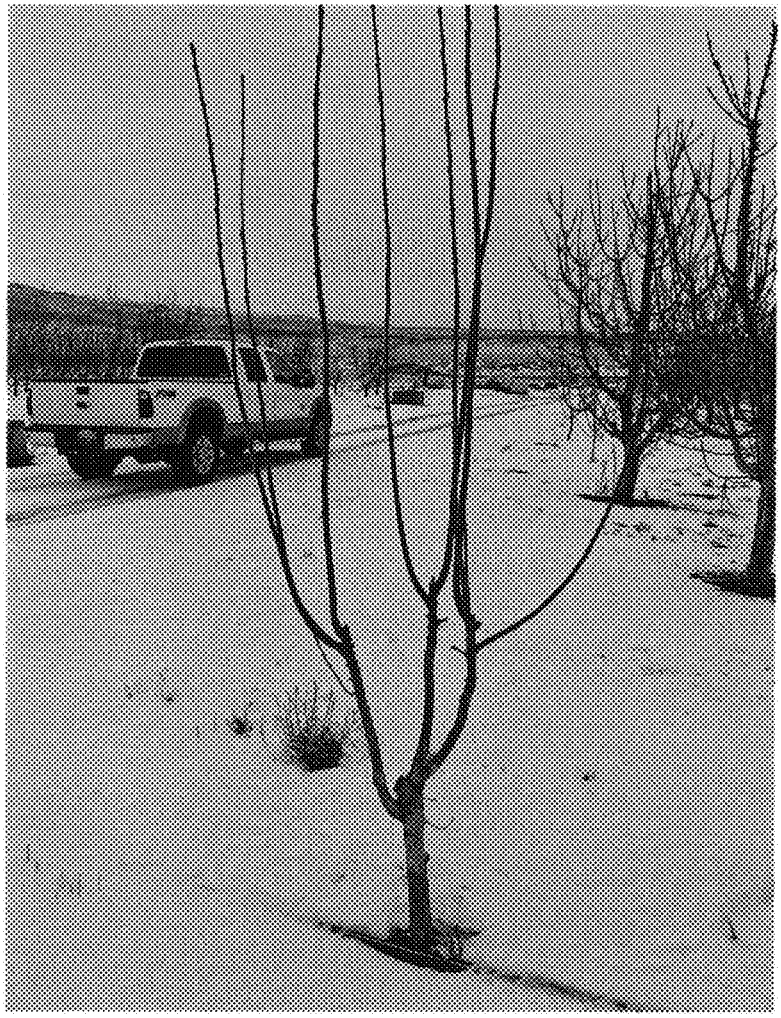
FIG. 1 is a photograph of a three-year-old 'RL 100' cherry tree without leaves or fruit.
Figure 2:
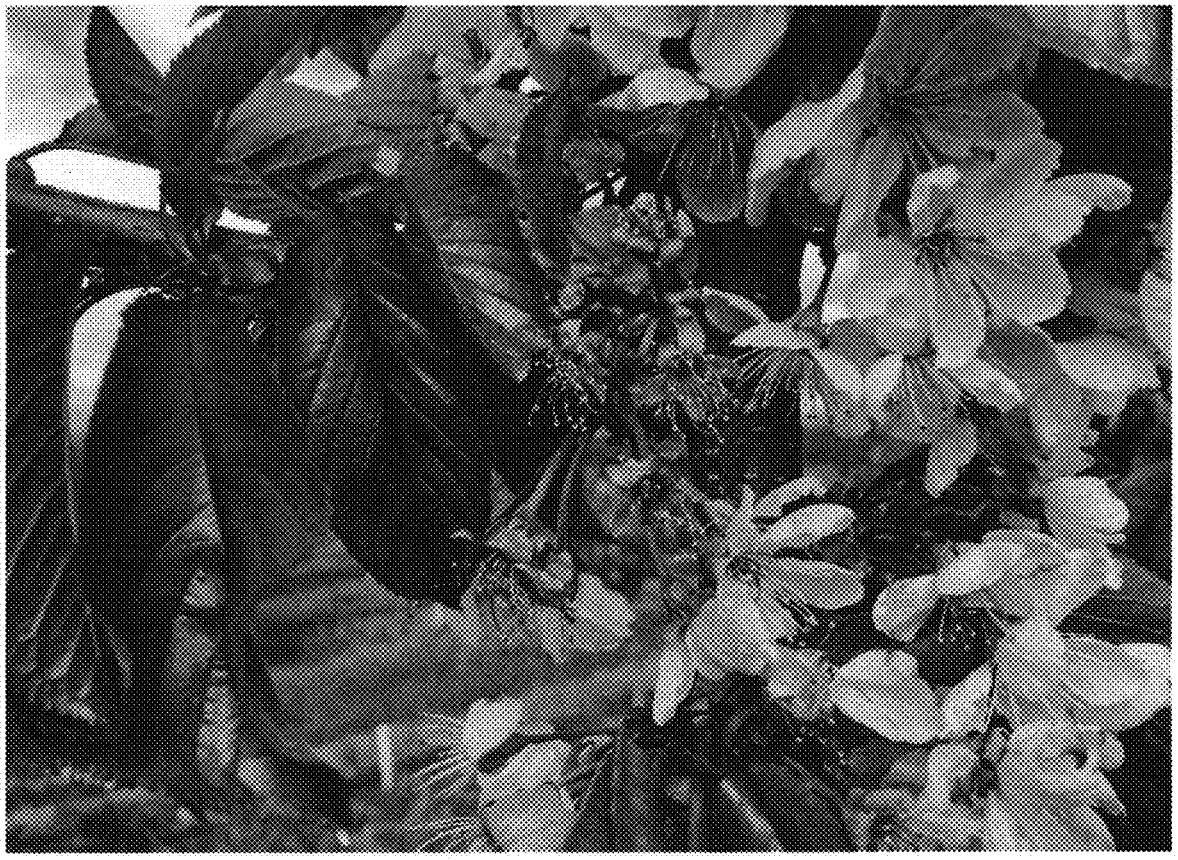
FIG. 2 is a photograph of blossoms and leaves on an 'RL 100' cherry tree.
Figure 3:
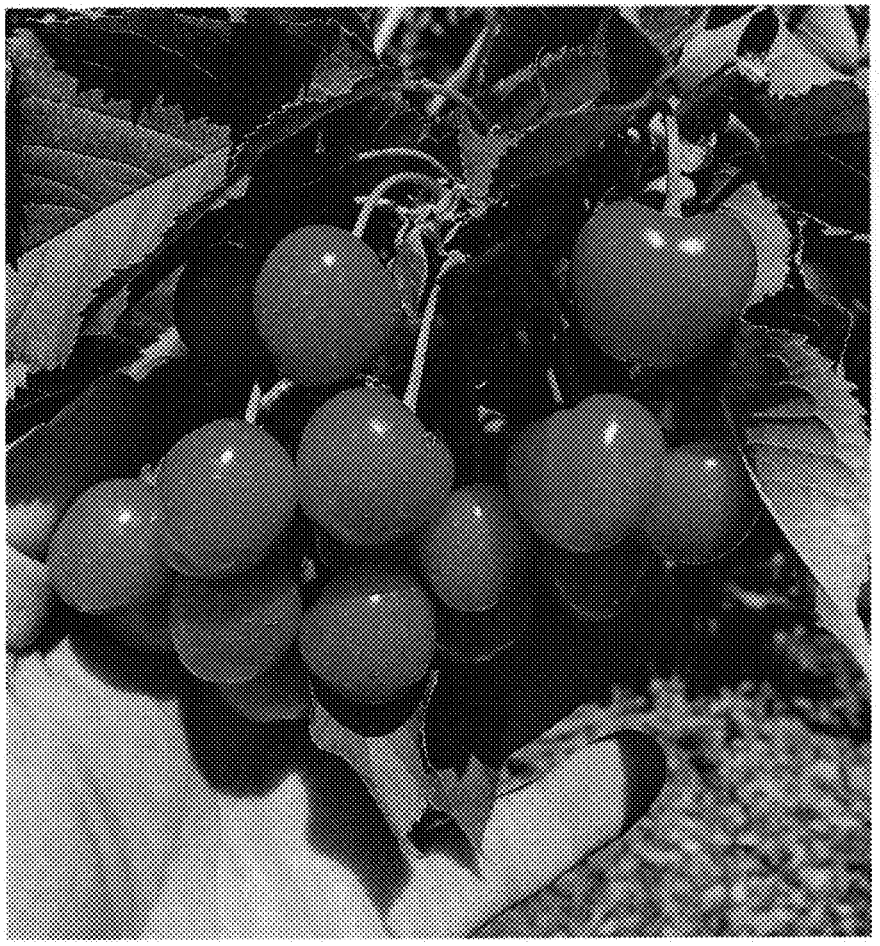
FIG. 3 is a photograph of cherries on an 'RL 100' cherry tree at veraison.
Figure 4:
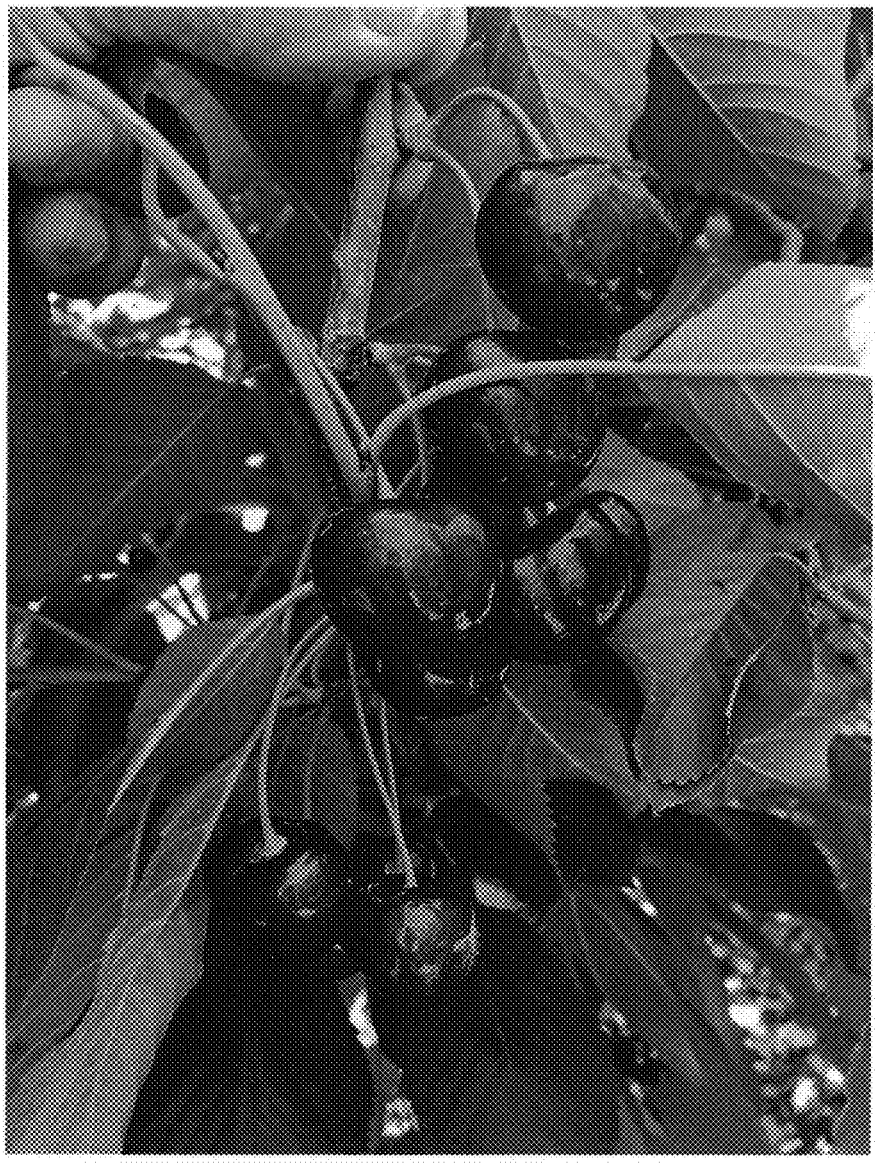
FIG. 4 is a photograph of ripe cherries on an 'RL 100' cherry tree.

The following detailed botanical description was recorded at Mattawa, Wash. during the 2013, 2014 and 2015 growing seasons (unless otherwise noted). The described trees were planted in 2013 (unless otherwise noted) and grown on Mazzard (not patented) rootstock. All colors are described with reference to The Royal Horticultural Society Colour Chart (First edition 1966). It should be understood that the characteristics described will vary somewhat depending upon cultural practices and climatic conditions, and will vary with location and season. Quantified measurements are expressed as an average of measurements taken from a number of individual plants of the new variety. The measurements of any individual plant or any group of plants of the new variety may vary from the stated average.

Tree:

*Vigor.*—Moderate.
*Habit.*—Upright and spreading.
*Density.*—Moderate to light.
*Spread of mature tree.*—5.5 m.
*Height.*—4.3 m.
*Trunk diameter* (*at* 30 *cm above the graft*).—16.5 cm.
*Bark texture.*—Mostly rough with some smooth areas.
*Bark color.*—Greyed-orange 166A.
*Scaffold limb diameter.*—52 mm to 95 mm, average 72 mm.
*Lenticel length.*—5.3 mm to 11.6 mm, average 8.7 mm.
*Lenticel color.*—Greyed-orange 166B.
*Branching.*—Weak to medium.

Branch (fruiting branches located at around 1 m above the graft union):
*Length.*—20 cm to 40 cm (2 and 3 year old wood).
*Diameter.*—8.1 mm to 13.8 mm, average 9.4 mm.
*Crotch angle.*—About 60°.
*Bark color.*—Purple N79A.
*Bark texture.*—Mostly rough with some smooth areas.
*Lenticel length.*—5.2 mm to 10.2 mm, average 7.4 mm.
*Lenticel color.*—Greyed-orange 175B.
One year old shoot:
*Length.*—14.3 to 17.8 mm, average 16 mm.
*Diameter.*—4.1 mm to 5.1 mm, average 4.8 mm.
*Internode length.*—4.3 cm.
*Color.*—Greyed-orange 175B.
*Lenticel diameter.*—0.3 mm to 0.5 mm.
*Lenticel shape.*—Round.
*Lenticel color.*—White 155A.
Flower buds:
*Quantity per spur.*—5 to 9, average 6.5 on 2+ year old spurs.
*Bud shape.*—Conical.
*Length.*—6.9 mm to 9.4 mm, average 8.1 mm.
*Diameter.*—3.9 mm to 4.9 mm, average 4.3 mm.
Flowers:
*Diameter of fully open flower.*—42.4 mm.
*Depth of fully open flower.*—5.9 mm.
*Relative position of petal margin.*—Touching to free.
*Number per cluster.*—2 to 4, average 3.1.
*Date of first bloom.*—Apr. 8, 2013.
*Date of full bloom.*—Apr. 13, 2013.
*Pollination requirement.*—Not self-fertile, pollinator required.
Petals:
*Number per flower.*—5.
*Length.*—18.5 mm.
*Width.*—17.1 mm.
*Petal shape.*—Circular to obovate, slightly elongated.
*Apex shape.*—Rounded, retuse.
*Base shape.*—Acute.
*Margin.*—Entire.
*Color of upper surface.*—White NN155D.
*Color of lower surface.*—White NN155D.
Pistil:
*Length.*—18.4 mm.
*Color.*—Yellow-green 153A.
Stigma:
*Diameter.*—0.6 mm.
*Color.*—Yellow-green 153A.
Style:
*Length.*—14.1 mm to 16.1, average 15.0 mm.
*Color.*—Yellow-green 153A.
Ovary:
*Length.*—2 mm to 4 mm.
*Color.*—Yellow-green 153A.
Stamens:
*Anther length.*—6.5 mm.
*Anther width.*—1.0 mm.
*Anther color.*—Yellow-orange 22B.
*Filament length.*—3.6 mm to 10 mm.
*Filament color.*—Yellow-green 145D.
*Pollen presence.*—Present, abundant.
*Pollen color.*—Orange 28B.
Pedicel:
*Length.*—18.5 mm.
*Diameter.*—2 mm to 3 mm.
*Color.*—Yellow-green 144A.
Sepals:
*Quantity.*—5.
*Length.*—7.7 mm.
*Width.*—4.8 mm.
*Color of upper surface.*—Yellow-green 144A.
*Color of lower surface.*—Yellow-green 146B.
*Sepal shape.*—Ovate, convex.
*Apex shape.*—Obtuse.
*Margin.*—Entire.
Leaves:
*Length.*—119 mm to 162 mm, average 145 mm.
*Width.*—47 mm to 67 mm, average 57 mm.
*Blade margin.*—Serrate, biserrate in places.
*Shape.*—Lanceolate.
*Apex.*—Acuminate.
*Base shape.*—Obtuse.
*Texture of upper surface.*—Glabrous, leathery.
*Leaf color.*—Upper surface — Yellow-green 147A.
*Leaf color.*—Lower surface — Yellow-green 147B.
Petiole:
*Length.*—29 mm to 41 mm, average 34.3 mm.
*Diameter.*—1.6 mm to 2.2 mm, average 1.9 mm.
*Color.*—Upper surface — Purple N79B.
*Color.*—Lower surface — Yellow-green 145C.
Glands:
*Length.*—3.0 mm.
*Width.*—1.8 mm.
*Color.*—Red-purple 63A.
Fruit:
*Quantity per cluster.*—1 to 3, mostly 2.
*Apical diameter.*—28.8 mm to 32.5 mm.
*Axial diameter.*—23.1 mm to 28.4 mm.
*Weight.*—12.5 g.
*Shape.*—Heart-shaped, asymmetric.
*Apex.*—Mostly rounded.
*Suture.*—Shallow to absent.
*Diameter of stalk cavity.*—11.7 mm to 14.1 mm.
*Depth of stalk cavity.*—2.0 mm to 6.0 mm.
*Stalk length.*—3.5 cm to 5.0 cm.
Skin:
*Thickness.*—0.05 to 0.10 mm.
*Texture.*—Smooth.
*Skin color of mature fruit.*—Red-purple 59A with red 45A speckles.
Flesh:
*Flesh texture.*—Smooth, uniformly crisp.
*Fibers.*—Moderate in numbers, not detectable in mouth.
*Aroma.*—Mild, typical of cherry.
*Brix.*—18.8°.
*Flesh color.*—Yellow-orange 19D.
*Firmness.*—Medium.
Stone:
*Length.*—10.4 mm to 12.1 mm, average 11.4 mm.
*Width.*—9.5 mm to 10.5 mm, average 10.0 mm.
*Shape.*—Oblong.
*Color.*—Greyed-orange 164C.
*Surface texture.*—Smooth with light undulations.
*Tendency to split.*—None observed.
Harvest:
*Harvest date.*—June 5 to June 25 (2021 season).
*Number of picks.*—1 pick.
*Harvest yield.*—20 pounds (7-year-old tree).
Disease resistance/susceptibility: None noted.
Pest resistance/susceptibility: None noted.
Storageability: Very good, up to 30 days under refrigeration.
Market use: Early season premium fresh market.
Shipping quality: Excellent.

The invention claimed is:

1. A new and distinct cherry tree named 'RL 100' substantially as described and illustrated herein.

* * * * *